(12) United States Patent
Fortuna et al.

(10) Patent No.: US 10,751,012 B2
(45) Date of Patent: *Aug. 25, 2020

(54) RADIOLOGICAL IMAGING DEVICE WITH IMPROVED MANEUVERABILITY

(71) Applicant: Imaginalis S.r.l., Sesto Fiorentino (Firenze) OT (IT)

(72) Inventors: Damiano Fortuna, Rignano sull'Arno (IT); Leonardo Manetti, Montevarchi (IT)

(73) Assignee: Imaginalis S.r.l., Sesto Fiorentino (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/220,791

(22) Filed: Dec. 14, 2018

(65) Prior Publication Data

US 2019/0125284 A1 May 2, 2019

Related U.S. Application Data

(63) Continuation of application No. 14/821,227, filed on Aug. 7, 2015, now Pat. No. 10,154,824.

(30) Foreign Application Priority Data

Aug. 7, 2014 (IT) .............................. MI2014A1459

(51) Int. Cl.
  *A61B 6/00* (2006.01)
  *A61B 6/03* (2006.01)
(52) U.S. Cl.
  CPC ............ *A61B 6/4447* (2013.01); *A61B 6/032* (2013.01); *A61B 6/4405* (2013.01); *A61B 6/4458* (2013.01); *A61B 6/547* (2013.01)
(58) Field of Classification Search
  CPC ..... A61B 6/4447; A61B 6/032; A61B 6/4405; A61B 6/4458; A61B 6/547
  See application file for complete search history.

(56) References Cited

U.S. PATENT DOCUMENTS

| | | | |
|---|---|---|---|
| 5,772,595 A | 6/1998 | Votruba et al. | |
| 6,234,672 B1 * | 5/2001 | Tomasetti | A61B 6/4405 378/197 |

(Continued)

FOREIGN PATENT DOCUMENTS

| | | |
|---|---|---|
| DE | 239099 C | 10/1911 |
| DE | 19725633 C1 | 12/1998 |

(Continued)

OTHER PUBLICATIONS

Dakin, S. G., et al., "Technical set-up and radiation exposure for standing computed tomography of the equine head," Equine Veterinary Education, vol. 26, No. 4, Apr. 1, 2014, pp. 208-225.

(Continued)

*Primary Examiner* — Courtney D Thomas
(74) *Attorney, Agent, or Firm* — Steptoe & Johnson LLP

(57) ABSTRACT

A radiological imaging device including a gantry suitable to perform the radiological imaging. The gantry includes a source suitable to emit radiation and a detector suitable to receive the radiation. The radiological imaging device further includes a control station suitable to control the functioning of the source and the detector. Also, the radiological imaging device includes an articulated arm suitable to move the gantry in relation to the control station to define various configurations. These configurations include an operating configuration wherein the gantry is distanced from the control station and a rest configuration wherein the gantry is alongside the control station limiting the overall dimensions of the device.

17 Claims, 6 Drawing Sheets

(56) References Cited

U.S. PATENT DOCUMENTS

| | | |
|---|---|---|
| 2003/0072416 A1 | 4/2003 | Rasche et al. |
| 2003/0097060 A1 | 5/2003 | Yanof et al. |
| 2004/0022350 A1 | 2/2004 | Gregerson |
| 2006/0029281 A1 | 2/2006 | Chen et al. |
| 2006/0149147 A1 | 7/2006 | Yanof et al. |
| 2008/0004523 A1 | 1/2008 | Jensen et al. |
| 2008/0255485 A1 | 10/2008 | Johnson et al. |
| 2009/0238432 A1 | 9/2009 | Can et al. |
| 2010/0172468 A1 | 7/2010 | Gregerson |
| 2010/0278300 A1 | 11/2010 | Yorkston et al. |
| 2011/0228910 A1 | 9/2011 | Gregerson et al. |
| 2011/0280364 A1 | 11/2011 | Maschke |
| 2011/0280379 A1 | 11/2011 | Maschke |
| 2013/0230135 A1 | 9/2013 | Hoshino et al. |
| 2013/0307969 A1 | 11/2013 | Gebauer |
| 2014/0098930 A1 | 4/2014 | Litzenberger et al. |
| 2015/0208993 A1 | 7/2015 | Stoutenburgh et al. |
| 2015/0320370 A1 | 11/2015 | Bouvier et al. |

FOREIGN PATENT DOCUMENTS

| | | |
|---|---|---|
| DE | 10208346 A1 | 9/2003 |
| DE | 102005054575 B3 | 4/2007 |
| DE | 102008019645 A1 | 10/2009 |
| DE | 102008019646 A1 | 10/2009 |
| DE | 102010011589 A1 | 9/2011 |
| EP | 0934730 A1 | 8/1999 |
| EP | 1875866 A2 | 1/2008 |
| GB | 2364646 A | 2/2002 |
| JP | S5786827 A | 5/1982 |
| JP | H02228946 A | 9/1990 |
| JP | H02297343 A | 12/1990 |
| JP | H0394737 A | 4/1991 |
| JP | 2002035017 A | 2/2002 |
| JP | 2009115468 A | 5/2009 |
| WO | 03070101 A1 | 8/2003 |
| WO | 2007022554 A3 | 3/2007 |
| WO | 2008144717 A1 | 11/2008 |
| WO | 2009083851 A1 | 7/2009 |
| WO | 2011058730 A1 | 5/2011 |
| WO | 2014001834 A1 | 1/2014 |
| WO | 2014001835 A1 | 1/2014 |
| WO | 2014058771 A1 | 4/2014 |
| WO | 2015052719 A1 | 4/2015 |
| WO | 2015054466 A1 | 4/2015 |
| WO | 2015112424 A1 | 7/2015 |
| WO | 2016201303 A1 | 12/2016 |
| WO | 2017134546 A2 | 8/2017 |

OTHER PUBLICATIONS

IT MI20141296 Written Opinion with Search Report dated Mar. 17, 2015.

IT MI20141297 Written Opinion with Search Report dated Mar. 23, 2015.

IT MI20141459 Written Opinion with Search Report dated Mar. 24, 2015.

IT MI20150264 Written Opinion with Search Report dated Oct. 19, 2015.

IT UB20154931 Written Opinion with Search Report dated Jun. 30, 2016.

IT UB20155187 Written Opinion with Search Report dated Jun. 30, 2016.

IT UB20155854 Written Opinion with Search Report dated Jul. 27, 2016.

IT UB20156291 Written Opinion with Search Report dated Aug. 23, 2016.

IT UB20160102 Written Opinion with Search Report dated Sep. 21, 2016.

IT UB20160047 Written Opinion with Search Report dated Sep. 28, 2016.

IT UA20163175 Written Opinion with Search Report dated Nov. 22, 2016.

IT UA20162689 Written Opinion with Search Report dated Dec. 12, 2016.

IT UA20163360 Written Opinion with Search Report dated Jan. 6, 2017.

IT 201600091340 Written Opinion with Search Report dated Jul. 20, 2017.

IT 201700042542 Written Opinion with Search Report dated Dec. 11, 2017.

* cited by examiner

RADIOLOGICAL IMAGING DEVICE WITH IMPROVED MANEUVERABILITY

CROSS-REFERENCE TO RELATED APPLICATIONS

This application is a continuation of U.S. patent application Ser. No. 14/821,227, filed Aug. 7, 2015, now U.S. Pat. No. 10,154,824, and claims the benefit of and priority to Italian Application No. MI2014A001459, filed Aug. 7, 2014, which are herein incorporated by reference in their entirety.

FIELD

The present disclosure relates to a radiological imaging device, and in particular, to a system and method for providing a radiological imaging device useful in the medical/veterinary sphere to obtain images of at least a portion of the internal anatomy of a patient, and then perform analyses, diagnoses or other assessments of the patient.

BACKGROUND

As is known, the radiological imaging devices currently available on the market have a standard structure including: a bed on which the patient is placed in order to perform image scanning of the patient and a gantry, which houses a source for emitting X-rays and a detector for receiving the X-rays.

Given the need to contain the source, the detector and the movement system, the gantry is cumbersome and, in particular, has a diameter of at least 1.5 meters and cannot therefore be maneuvered through doors or other passages present in a hospital. For that reason, if radiological imaging needs to be performed to verify the successful outcome of an operation, the patient must be lifted from the operating table, placed on a bed, moved to another part of the hospital to the room where the imaging device is installed, lifted again and then placed on the bed of the radiological imaging device. This procedure may be further complicated if the radiological imaging reveals the need for further surgery, in which case, the patient would need to be taken back to the operating room. Additionally, such maneuvers often entail problems for the patient and therefore need to be performed with particular care and expertise. Consequently, the length of time needed to perform the aforementioned maneuvers increases.

SUMMARY

Existing limitations associated with the foregoing, as well as other limitations, can be overcome by a method for operating a radiological imaging device, and by a system, apparatus, and computer program that operates in accordance with the method. Briefly, and in general terms, the present disclosure is directed to various embodiments of a radiological imaging device.

The radiological imaging device includes a gantry suitable to perform the radiological imaging. The gantry has a source suitable to emit radiation and a detector suitable to receive the radiation. Further, the radiological imaging device includes a control station suitable to control the functioning of the source and the detector. Also, the radiological imaging device includes an articulated arm suitable to move the gantry in relation to the control station defining various configurations. These configurations include, for example, an operating configuration wherein the gantry is distanced from the control station and a rest configuration wherein the gantry is alongside the control station limiting the overall dimensions of the radiological imaging device.

In one embodiment, the gantry defines a preferred axis of expansion and the control station defines a main axis of extension. In the rest configuration, the preferred axis of expansion is substantially parallel to the main axis of extension. In this embodiment, the preferred axis of expansion substantially coincides with the main axis of extension in the rest configuration.

In yet another embodiment, the articulated arm includes a first body joined to the control station, a second body joined to the gantry, and a hinge suitable to command the relative rotation between the bodies along an axis of rotation. In this embodiment, the axis of rotation is substantially perpendicular to the main axis of extension. Further, the articulated arm may include a rotation mechanism positioned between the gantry and second body so as to rotate the gantry in relation to the second body. It has been contemplated that the axis of rotation is perpendicular to the preferred axis of expansion in this embodiment. In other embodiments, the articulating arm may be formed using multiple arm segments. Then, multiple hinges or other types of rotational mechanisms may be disposed at each joint between the multiple arm segments.

In one embodiment, the control station may include a linear actuator suitable to move the articulated arm and the gantry in a direction substantially parallel to the main axis of extension.

The radiological imaging device also may include a carriage suitable to be joined to the control station permitting the movement of the radiological imaging device. In this embodiment, the carriage includes at least one caterpillar track.

The various embodiments of the radiological imaging device permit the patient to be maneuvered easily and reduces risks to the patient. Further, the radiological imaging device may permit a reduction in the maneuvers involving the patient.

Other features and advantages will become apparent from the following detailed description, taken in conjunction with the accompanying drawings, which illustrate by way of example, the features of the various embodiments.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5a shows a different embodiment of the subassembly of FIG. 4a;

DETAILED DESCRIPTION

Figure 1A:
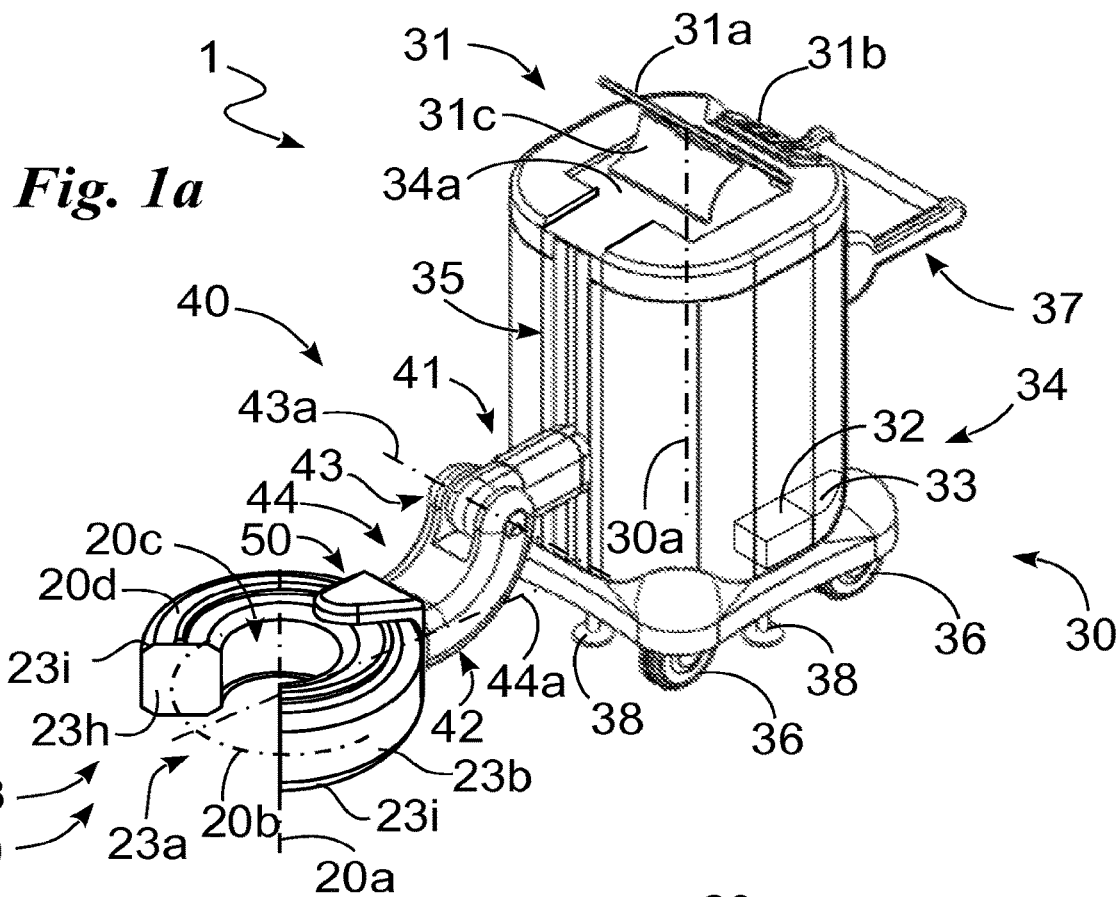
FIGS. 1a-1b show examples of the radiological imaging device in some of its possible configurations.

Each of the features and teachings disclosed herein can be utilized separately or in conjunction with other features and teachings to provide a radiological imaging system occupying a reduced space. Representative examples utilizing many of these additional features and teachings, both separately and in combination are described in further detail with reference to the attached figures. This detailed description is merely intended to teach a person of skill in the art further details for practicing aspects of the present teachings and is not intended to limit the scope of the claims. Therefore, combinations of features disclosed above in the detailed description may not be necessary to practice the teachings in the broadest sense, and are instead taught merely to describe particularly representative examples of the present teachings.

In the description below, for purposes of explanation only, specific nomenclature is set forth to provide a thorough understanding of the present disclosure. However, it will be apparent to one skilled in the art that each of these specific details are not required to practice the teachings of the present disclosure.

Moreover, the various features of the representative examples may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure. It is also expressly noted that the dimensions and the shapes of the components shown in the figures are designed to help to understand how the present teachings are practiced, but not intended to limit the dimensions and the shapes shown in the examples. In this document, measurements, values, shapes, angles, and geometric references (such as perpendicularity and parallelism), when associated with words like "about" or other similar terms such as "approximately" or "substantially," should be construed to allow for measurement errors or others errors due to production and/or manufacture process, and may vary by up to ten percent.

With reference to the drawings, reference numeral 1 globally denotes a radiological imaging device. The radiological imaging device 1 is useful in both the medical and veterinary spheres for performing radiological imaging of at least one portion of the internal anatomy of a patient. In particular, the radiological imaging device 1 is useful for performing X-rays, CAT or CT scans, fluoroscopy and other radiological imaging examinations.

In one embodiment, the radiological imaging device 1 includes a gantry 20 suitable to perform the radiological imaging. There is also a control station 30 suitable to control the functioning of the gantry 20 and the control station defines a main axis of extension 30a as shown in FIG. 1a. The device includes an articulated arm 40 suitable to fasten and to move the gantry 20 in relation to the control station 30.

The gantry 20 has an annular shape substantially defining a preferred axis of expansion 20a. The gantry also may have a circular trajectory of expansion 20b having its center on the axis 20a. An analysis zone 20c of the gantry is suitable to contain the portion to be analyzed. In one embodiment, the gantry includes two base surfaces 20d having a circular crown cross-sectional profile. Preferably, the base surfaces 20d are substantially perpendicular to the preferred axis of expansion 20a.

In one embodiment, the gantry 20 has an external diameter less than about 1000 mm. In other embodiments, the gantry 20 has an external diameter less than about 850 mm, or equal to about 750 mm.

Figure 4A:
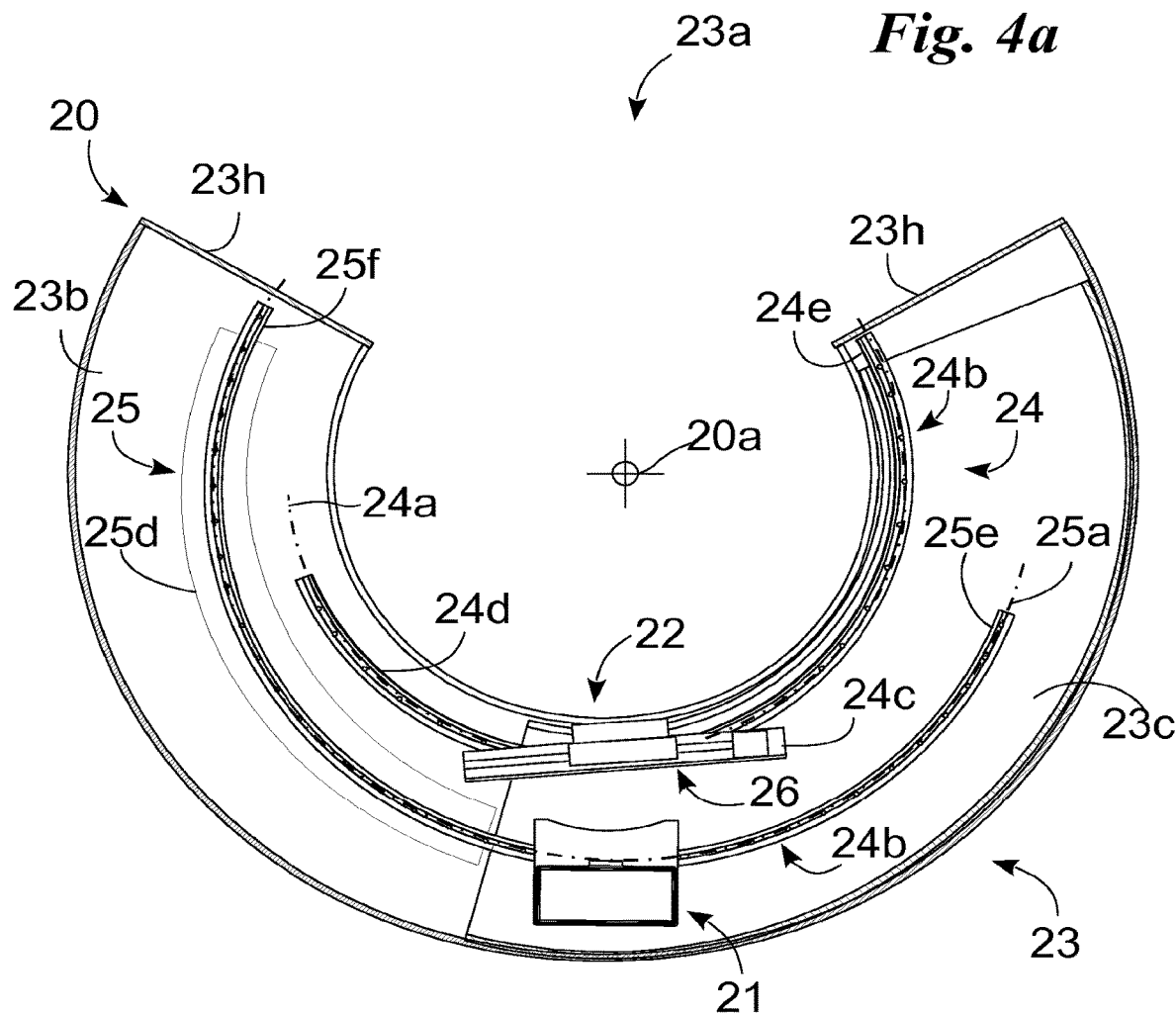
FIG. 4a shows a subassembly of the radiological imaging device according to the invention.
Figure 4B:
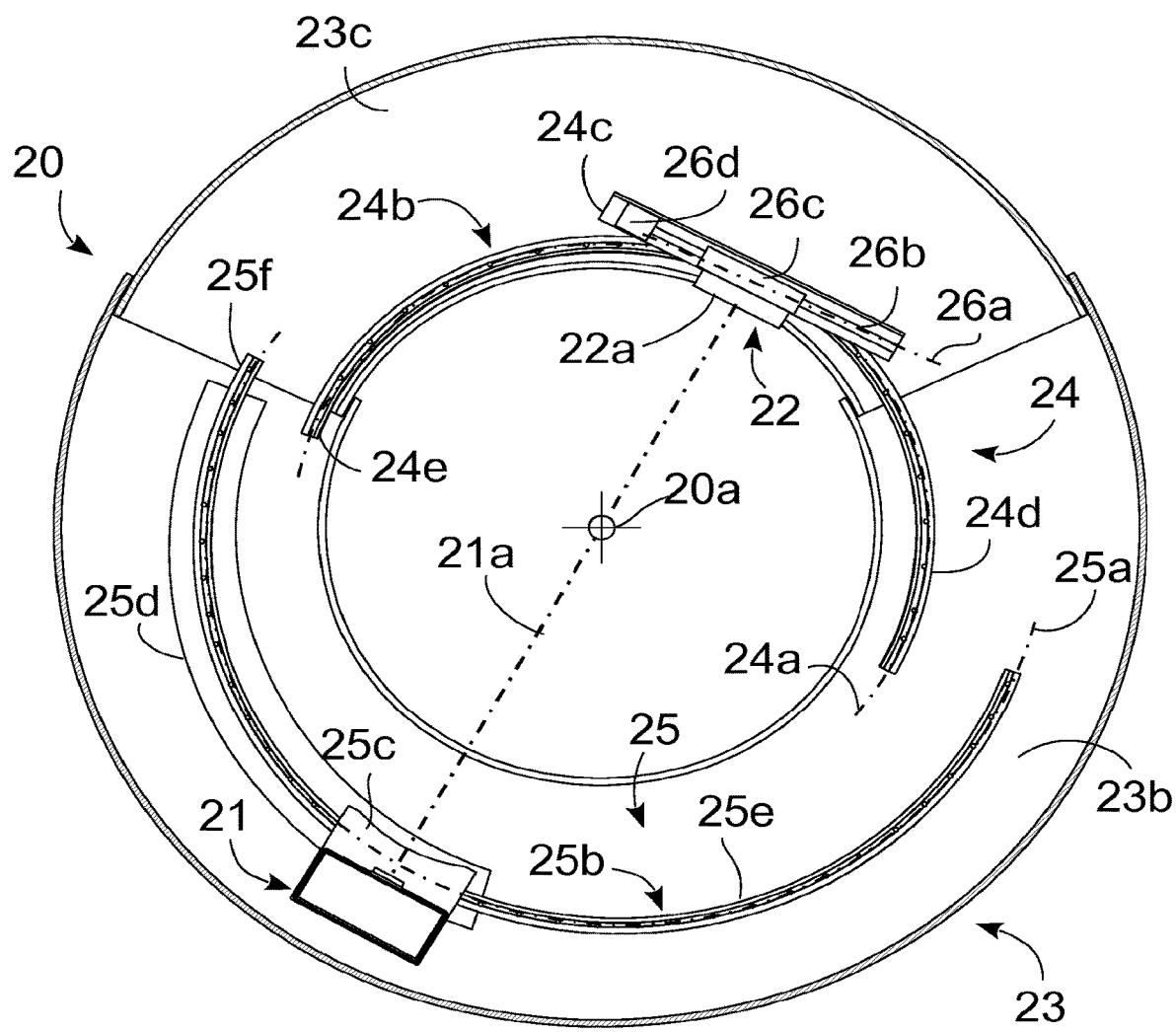
FIG. 4b shows the subassembly of FIG. 4a in a different configuration.

The gantry 20 includes a source 21 (FIG. 4a) suitable to emit radiation, such as X-rays. As shown in FIG. 4b, the gantry 20 defines a central axis of propagation 21a, which may be substantially perpendicular to the preferred axis of expansion 20a. Referring again to FIG. 4a, the gantry includes a detector 22 defining a sensitive surface 22a suitable to receive the radiation from the source 21. There is at least one internal mover able to rotate the source 21 and/or the detector 22 around the preferred axis of expansion 20a. The gantry also includes a casing 23 suitable to house the source 21, the detector 22 and the mover.

Figure 5A:
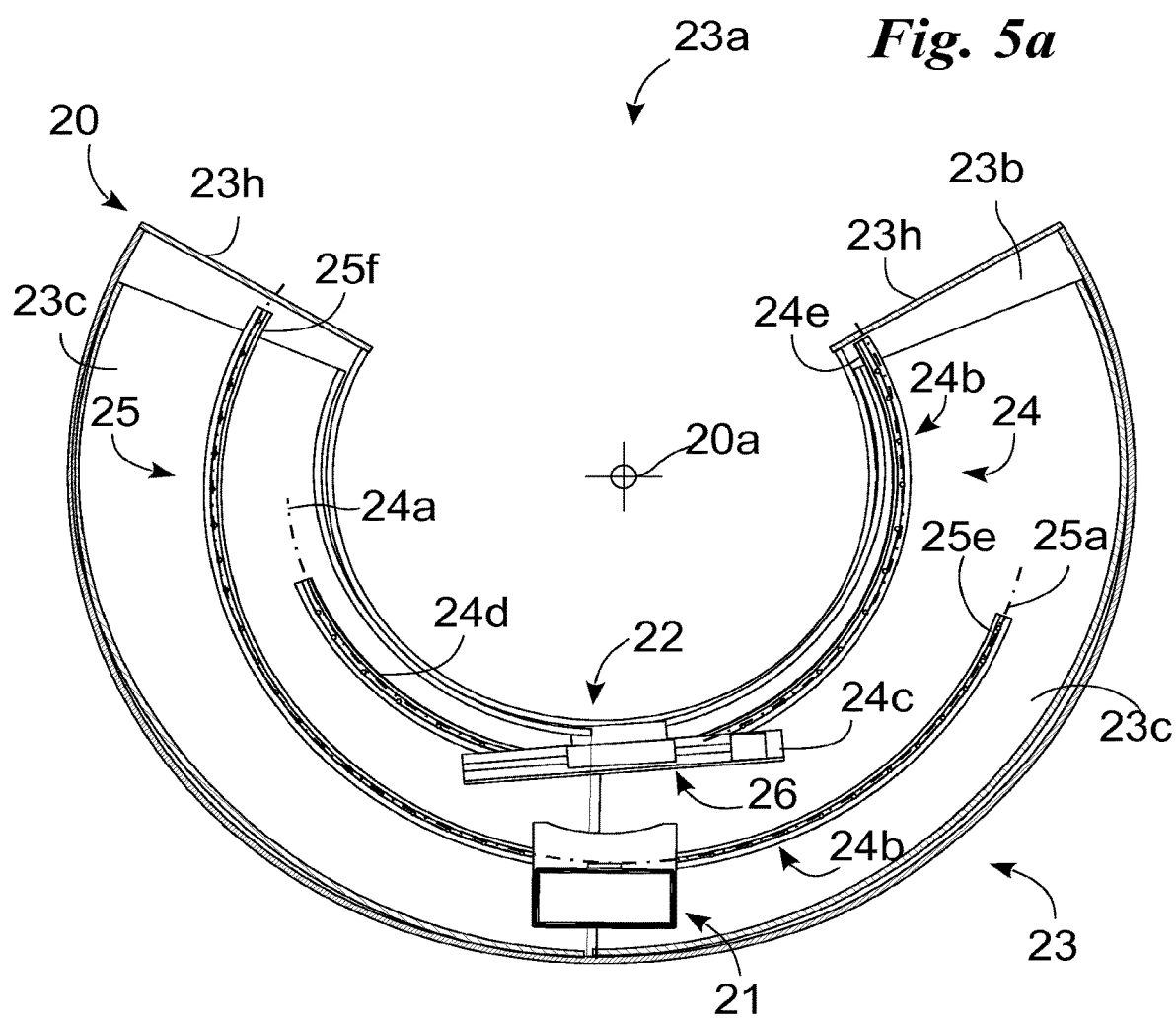

The casing 23 forms the outer body of the gantry 20 and, therefore, it defines the dimensions and, in particular, the angular extension of the gantry 20. The casing 23, in order to facilitate the insertion of the portion of the patient to be analyzed in the analysis zone 20c, presents an annular shape opened in order to define an angular perimetric aperture 23a as shown in FIG. 5a. Through the angular perimetric aperture 23a, it is possible to introduce into the analysis zone 20c a patient's portion by a radial/perpendicular motion of the casing 23 or of the patient's portion with respect to the axis of expansion 20a.

In one embodiment, the casing 23 includes a curved module 23b joined to the articulated arm 40 and being in the shape of an arc of a circumference extending along the circular trajectory of expansion 20b and having an angular extension approximately between 180° and 300°, preferably, approximately between 230° and 270° and, more preferably, approximately between 240° and 250° in order to define an angular aperture 23a of about 120° and about 110°.

In one embodiment, the casing 23 and, therefore, the gantry 20 are of the telescopic type, and suitable to vary the angular extension of the casing 23 and the gantry 20 defining, for the imaging device 1, at least one rest configuration and at least a working configuration.

In the rest configuration (FIGS. 1a, 1b, 4a and 5a), the casing 23 and the gantry 20 are contracted and have minimal angular dimensions. As shown in the figures, the gantry and the curved module 23b have substantially a "C" shape. Therefore, in this rest configuration, the casing 23 and the gantry 20 define an arc of a circumference substantially centered on the axis of expansion 20a and having an angular extension approximately equal to the angular extension of the curved module 23b, which is described in detail above. In this configuration the gantry partially surrounds a portion of the patient.

In the at least one working configuration (FIGS. 2, 4b and 5b) the casing 23 and the gantry 20 have an angular extension greater than in the rest configuration and, therefore, of the curved module 23b. In one embodiment, the working configuration the casing 23 and, therefore, the gantry 20 have an angular extension of substantially 360°.

In order to define the configurations, the casing 23 includes, in addition to the module 23b, at least an additional curved module 23c being in the shape of an arc of a circumference centered on the axis 20a and extending along the circular trajectory of expansion 20b. The casing also includes at least a kinematic expansion mechanism 23d suitable to move the additional curved module 23c with respect to the curved module 23b along the circular trajectory of expansion 20b so as to allow the casing 23 to assume any angular extension between 360° and the angular extension of the curved module 23b.

The additional curved module 23c has a cross-section different from that of the curved module 23b so as to at least partially overlap the curved module 23b. In detail, the additional module 23c has a cross-section smaller than that of the curved module 23b so as to be housed inside it. The additional curved module 23c has an angular extension approximately between 40° and 180°, preferably, approximately between 80° and 140° and, more preferably, approximately between about 130° and about 110°.

Figure 5B:
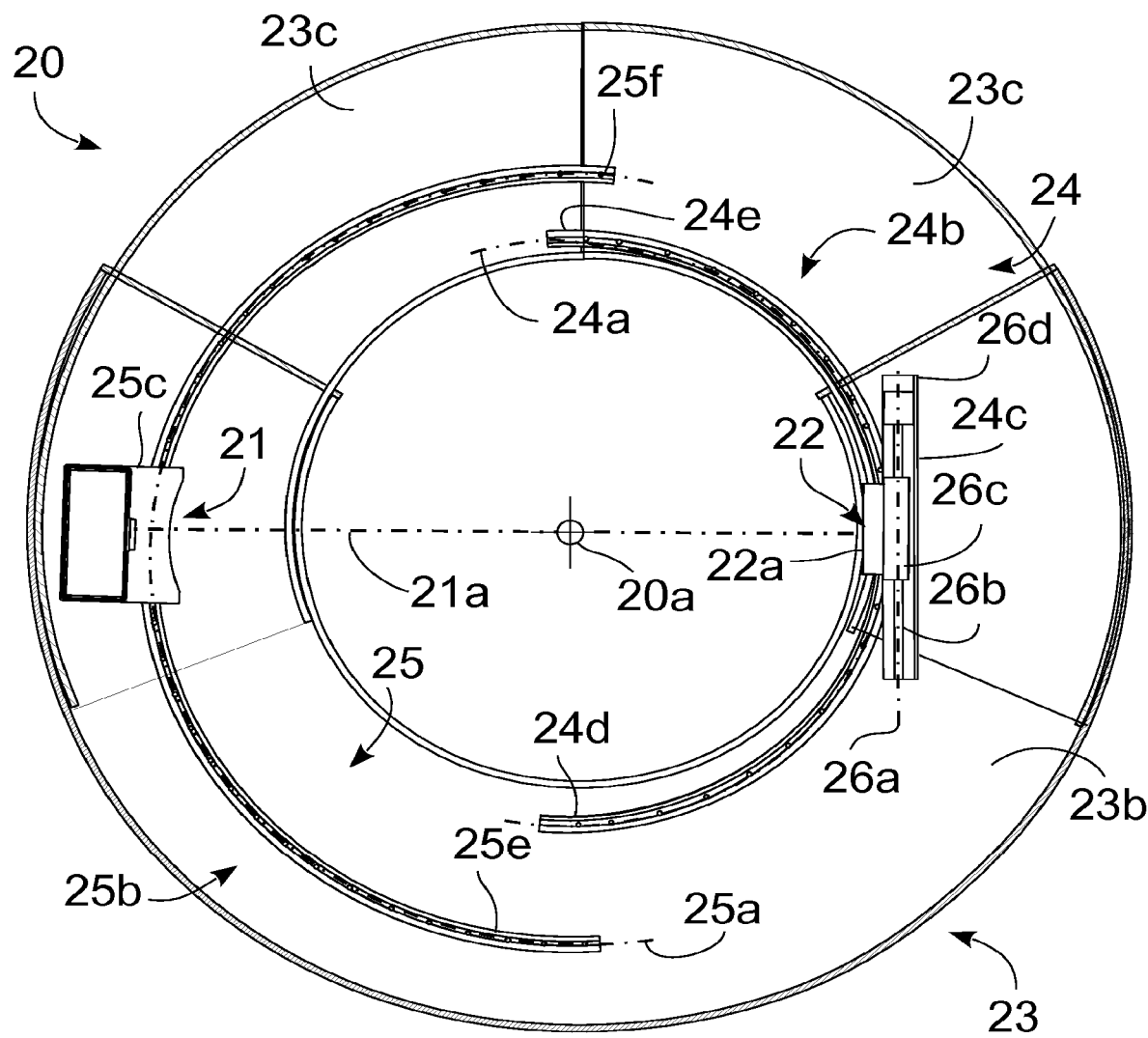
FIG. 5b shows the subassembly of FIG. 5a in a different configuration.

In certain embodiments (FIGS. 5a and 5b), the casing 23 includes a curved module 23b, two additional curved modules 23c disposed at opposite ends of the curved module 23b and substantially symmetrical between each other. In these embodiments, the casing includes a kinematic expansion mechanism 23d able to move, preferably independently from each other, the two additional modules 23c respect to the curved module 23b along the circular trajectory of expansion 20b and in opposite directions so that the additional curved modules 23c reach a mutual contact inside the module 23b in the rest configuration (FIG. 5a) and outside the module 23b in the working configuration (FIG. 5b). The curved modules 23c may be moved manually with respect to curved module 23b.

As shown in FIGS. 5a and 5b, the additional curved modules 23c have a cross-section different from that of the curved module 23b so as to at least partially overlap the curved module 23b. In one embodiment, the additional modules 23c have a cross-section smaller than that of the curved module 23b so as to be housed inside it. In one example, the additional curved modules 23c have an angular extension approximately between 30° and 120°, preferably, approximately between 45° and 100° and, more preferably, approximately between about 60°-70°.

The kinematic expansion mechanism 23d is adapted to move the additional curved module 23c with respect to the curved module 23b so as to vary the extension of the portion of the additional module 23c superimposed and, in particular, included inside the arched module 23b. In one embodiment, the mechanism 23d is adapted to arrange, in the rest configuration (FIG. 4a), the additional curved module 23c totally located inside in the curved module 23b so that the angular extent of the gantry 20 is substantially equal to that of the curved module 23b.

In contrast, in the working configuration (FIG. 4b), the kinematic expansion mechanism 23d allows the curved module 23c to protrude from the curved module 23b so that the angular extent of the gantry 20 is greater than the one of the curved module 23b and, substantially equal to that of the curved module 23b plus the angular extent of the portion of additional module 23c protruding from the curved module 23b.

Figure 6:
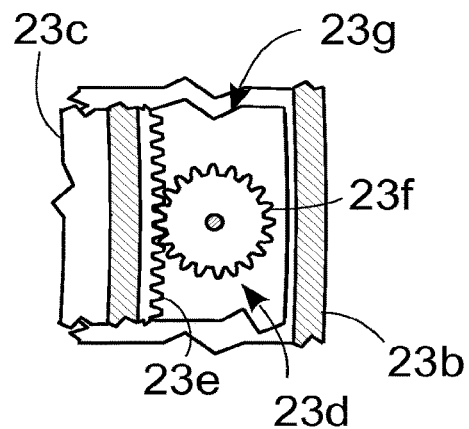
FIG. 6 shows a kinematic mechanism according to an example embodiment herein.

The kinematic mechanism 23d (FIG. 6) is mechanical and, for example, comprises at least one rack 23e substantially disposed on an additional module 23c and substantially extending along the circular trajectory of expansion 20b. The kinematic mechanism 23d also may include at least one motorized toothed wheel 23f hinged to the curved module 23b, engaging with the racks 23e so as to control the motion of the additional module 23c along the circular trajectory of expansion 20b. Alternatively, the mechanism 23d can move an additional module 23c with respect to the module 23b through belts, arched actuators, or, in a further alternative, it can be of magnetic type.

In one embodiment, in order to hide the kinematic expansion mechanism 23d between the modules 23b and 23c, the additional curved module 23c is provided with a recess defining a housing channel 23g for the kinematic mechanism 23d. Additionally, the casing 23 may include bulkheads 23h or other similar elements integrally or removably attached to the ends of the curved module 23b so as to prevent access of dirt, blood, debris, or other substance in gantry 20. Further, the casing may include a motor, not shown in the drawings, suitable to move the bulkheads 23h with respect to the ends of the curved module 23b and, thus, of the gantry 20. In one example, the motor is an electric motor and moves the bulkheads 23h by means of a rotational movement with respect to an axis substantially perpendicular to the circular trajectory 20b. It has been contemplated that the motor can by any type of motor suitable to move the bulkheads.

In certain embodiments, to prevent shocks/collisions from damaging the gantry 20, the casing 23 and, in particular, the curved module 23b may include a coating 23i of the curved module 23b made of elastomeric material or other similar material suitable to absorb the shocks/collisions. The coating 23i may be in the form of strips which at least partially cover the external surface of the casing 23 and, in detail, disposed on the casing 23 at least along its edges facing the analysis region 20c and/or its edges in the opposed side.

In order to configure the gantry 20 in the above-described configurations keeping the source 21 and the detector 22 and the at least one internal mover always inside the gantry 20, the gantry 20 includes at least one internal mover having an angular extension substantially below the angular extension of the curved module 23b. In one embodiment, the at least one internal mover has an angular extension between the angular extension of the curved module 23b and the angular extension of the additional curved module 23c.

In one embodiment, in order to move the source 21 and the detector 22 in an independent manner, the gantry 20 includes an internal inner mover 24 defining, for the detector 22, an inner sliding trajectory 24a. The gantry also may include an internal outer mover 25 defining, for the source 21, an outer sliding trajectory 25a distinct from the inner sliding trajectory 24a. The sliding trajectories 24a and 25a each have a circular shape with their center on the axis of expansion 20a so as to move the source 21 and/or the detector 22 without substantially changing their distances from the preferred axis of expansion 20a. Preferably, the sliding trajectories 24a and 25a lie on a single plane substantially perpendicular to the preferred axis of expansion 20a.

In detail, the outer sliding trajectory 25a defines a distance from the source 21 to the axis of expansion 20a, and the inner sliding trajectory 24a defines a distance from the detector 22, i.e. the sensitive surfaces 24a, to the axis of expansion 20a. The radius defined by the outer sliding trajectory 25a is greater than the radius defined by the inner sliding trajectory 24a. In one embodiment, the outer sliding trajectory 25a defines a distance from the source 21 to the axis of expansion 20a between about 500 mm and about 50 mm. This distance may also be between about 350 mm and about 50 mm and, or between about 250 mm and about 100 mm. While the inner sliding trajectory 24a defines a distance from the sensitive surface 22a to the preferred axis of expansion 20a between about 400 mm and about. This distance may also be between about 300 mm and about 25 mm, or between about 150 mm and about 75 mm.

In one embodiment, the internal movers 24 and 25 include an arched guide and at least a cart adapted to move it along the arched guide. By way of example, the internal inner mover 24 includes an inner arched guide 24b jointly fixed to the additional curved module 23c and defining the sliding trajectory 24a. The inner mover 24 also includes at least one inner cart 24c. The inner cart 24c may be motorized (e.g., electric, preferably of recirculating ball type). The inner cart 24c may be constrained to the detector 22 and adapted to move it along the inner arched guide 24b and, therefore, along the inner trajectory 24a.

In one embodiment, the internal outer mover 25 includes an arched outer guide 25b jointly fixed to the curved module 23b and defining the sliding trajectory 25a. The internal outer mover 25 also includes at least one outer cart 25c. The at least one outer cart 25c may be motorized (e.g., electric, preferably of recirculating ball type). The internal cart 25c constrained to the source 21 and adapted to move it along the outer arched guide 25b and, therefore, along the outer trajectory 25a.

Additionally, the internal outer mover 25 includes a shim 25d (FIGS. 4a and 4b) disposed between the outer guide 25b and the curved module 23b. The shim has a thickness substantially at least equal to the thickness of the additional module 23c in order to space and to raise the arched outer mover 25b from the curved module 23b. This allows the additional module 23c to be inserted between the outer guide 25b and the curved module 23b bringing the gantry 20 in the contracted configuration (as hereinafter described). Alternatively, if the gantry 20 is provided with two additional modules 23c (FIGS. 5a and 5b), the internal outer mover 25 does not include a shim 25d and the second guide 25d is directly integral bound to a second additional module 23c distinct from the additional module which is integral with the inner guide 24b.

In one embodiment, each arched guide 24b and 25b has an angular extension at least equal to 180° so that the internal movers 24 and 25 are able to rotate the source 21 and/or the detector 22 by an angle between 0° and almost 180°. In one example, the arched guides 24b and 25b have an angular extension between about 180° and about 210°. The angular extension of the arched guides 24b and 25b may also be between about 190° and about 200°.

The inner arched guide 24b is jointly bound to the additional curved module 23c so as to define, on opposite sides of and with respect to the additional module 23c, a first inner protruding portion 24d and a second inner protruding portion 24e. The portions 24d and 24e may be cantilevered with respect to the additional curved module 23c.

Figure 3:
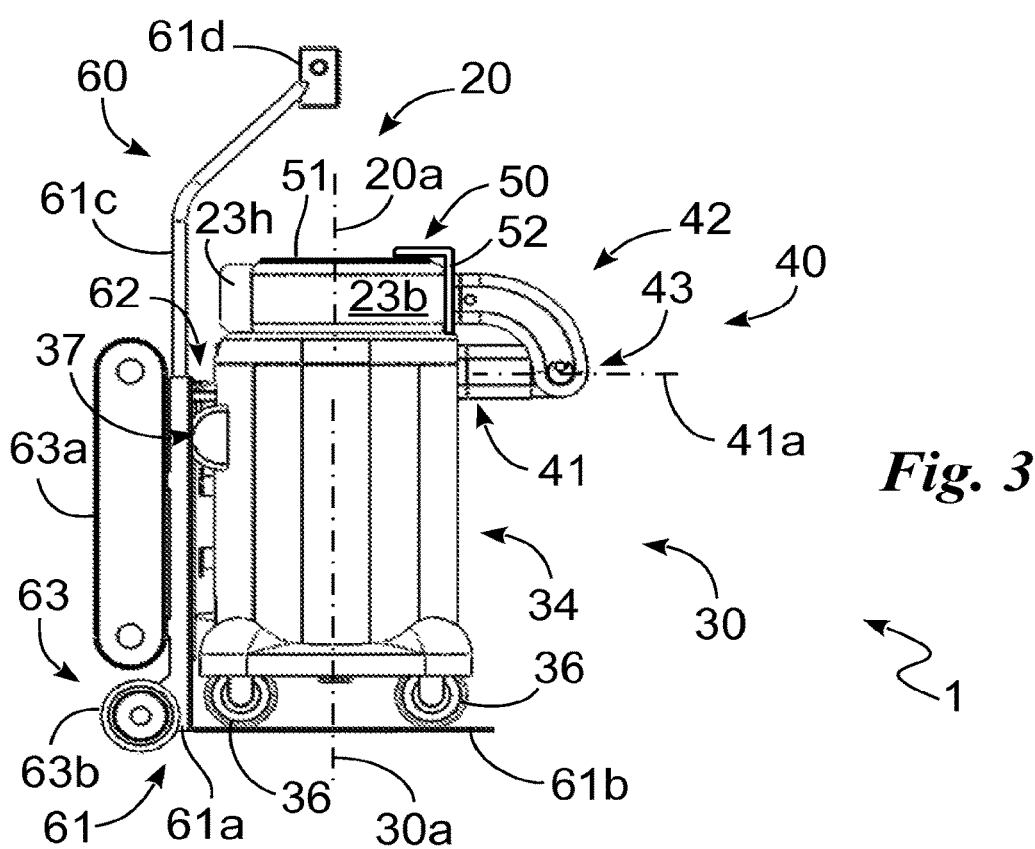
FIG. 3 shows the radiological imaging device according to an example embodiment.

The outer arched guide 25b is jointly bound to the shim 25d so as to define, on opposite sides of and with respect to the shim 25d, a first outer protruding portion 25e and a second outer protruding portion 25f. In the rest configuration (FIG. 4a), the first outer portion 25e is superimposed to the additional curved module 23c and the second outer protruding portion 25f is cantilevered with respect to the shim 25d. In the working configuration of maximum extension (FIG. 3b), the first outer protruding portion 25e is cantilevered with respect to the shim 25d and the second outer protruding portion 25f is superimposed to the additional curved module 23c.

In one embodiment, the first protruding portions 24d and 25e and the second protruding portions 24e and 25f respectively have an angular extension equal to approximately 90° and approximately 10° to 20°.

Alternatively, the internal mover 24 and 25 may be movable with respect to the respective modules 23b and 23d so as to move, suitably by an angle between about 0° and about 180°, the source/detector by a movement of the guides 24b and 25b with respect to the modules 23b and 23c along the trajectories 24a and 25a.

Each mover 24 and 25 includes, in addition to the guide 24b and 25b, and the cart 24c and 25c, a steering mechanism able to command and to move along the sliding trajectories 24a and 25a each of the arched guides 24b and 25b with respect to the modules 23b and 23c. The movers 24 and 25 may also include a driving block able to drive the sliding of the guides 24b and 25b along the trajectory 24a and 25a. The steering mechanism defines, for each of the movers 24 and 25, an overlap configuration where guides 24b and 25b completely overlap the corresponding module 23b and 23c, respectively. Also, the steering mechanism defines a cantilevered configuration where the guides 24b and 25b partially protrude from the respective module 23b and 23c respectively.

In one example, the steering mechanism of the inner mover 24 is adapted to move the arched guide 24b using a magnetic field. In this example, the steering mechanism of the inner mover 24 includes permanent magnets integral with the guide 24b, and an magnetic emitter integral to the module 23b and/or 23c and able to emit a magnetic field commanding the arched guide 24b by interacting with the permanent magnets. Alternatively, the steering mechanism is adapted to mechanically move the guide 24b and, for example, include a rack integral with the arched guide 24b and at least one toothed motorized wheel hinged to form module 23b and/or 23c and able to engage with the rack.

In one example, the steering mechanism of the outer mover 25 is adapted to move the arched guide 25b using a magnetic field. In this example, the steering mechanism includes permanent magnets integral with the guide 25b, and an magnetic emitter integral to the corresponding module 23b and/or 23c and able to emit a magnetic field commanding the arched guide 24b by interacting with the permanent magnets. Alternatively, the steering mechanism is adapted to mechanically move the corresponding guide 25b and, for example, include a rack integral with the arched guide 25b and at least one toothed motorized wheel hinged to form module 23b and/or 23c and able to engage with the rack.

The driving block of each mover 24 and 25 may include one or more idler wheels hinged to the module 23b or 23c and adapted to go in contact with the guide 24b or 25b. The driving block of each mover 24 and 25 also includes a pilot profile bound integrally with the module 23b or 23c on the side opposite to the idler wheels relative to the arched guide 24b or 25b in order to enclose the arched guide between the idler wheels and the pilot profile. The pilot profile extends substantially along the sliding trajectory 24a or 25a and is shaped so as to go in contact with the arched guide 24b or 25b and to guide the scrolling of the guide.

In this case, each guide 24b and 25b has an angular extension at least equal to 90°. In one embodiment, the arched guides 24b and 25b has an angular extension between about 90° and about 120°. The angular extension of the arched guides 24b and 25b may also be between about 95° and about 110°.

In an another embodiment, the internal movers 24 and 25 are telescopic so as to move, suitably an angle between about 0° and about 180°, the source 21 and/or detector 22 by means of a variation of its extension along the sliding trajectory 24a and/or 25a.

Therefore, the internal inner mover 24 may include the above-described arched guide 24b, the cart 24c, the steering mechanism, the driving block and, in addition, an additional guide arched extending almost along the sliding trajectory 24*a*, having a lower section than the arched guide 24*b* and located between the arched guide 24*b* and the cart 24*c* so that the cart 24*c* runs on it. The internal inner mover 24 may also include a command group adapted to move along one of the inner trajectory 24*a* the additional arched guide with respect to the arched guide 24*b* in order to vary the extension of the mover 24. At the same time, the outer mover 25 may include the above-described arched guide 25*a*, the cart 25*c*, the steering mechanism, the driving block and, in addition, an additional guide arched extending almost along the sliding trajectory 25*a*, having a lower section than the arched guide 25*b* and located between the arched guide or 25*b* and the cart 25*c* so that the cart 25*c* runs on it. The outer mover 25 also may include a command group adapted to move along one of the trajectory 25*a* the additional arched guide with respect to the guide 25*b* in order to vary the extension of the mover 25.

The command groups and the steering mechanisms define, for each internal mover 24 and 25, a contracted configuration in which the additional guide arched is superimposed on the corresponding guide 24*b* and 25*b* which, in turn, is superimposed on the corresponding module 23*b* and 23*c*. Also, the command groups and the steering mechanisms may define an intermediate configuration in which the additional guide at least partially protrudes by the guide 24*b* and 25*b* or the guide 24*b* and 25*b* at least partially protrudes by the module 23*b* and 23*c*. The command groups and steering mechanisms may define an expanded condition in which the additional guide at least partially protrudes by the corresponding guide 24*b* and 25*b* which, in turn, at least partially protrude by the corresponding module 23*b* and 23*c*.

In one example, the command group can be of the magnetic type and include permanent magnets integral with the additional guide. The command group may also include one or more magnetic emitters integral with the guide 24*b* and 25*b* and able to emit a magnetic field which interacts with the permanent magnets so as to control the translation along the trajectory 24*a* or 25*a* of the additional guide. Alternatively, the command group is of a mechanical type and includes a rack integral on the additional guide, at least one motorized toothed wheel hinged to the arched guide 24*b* and 25*b* and adapted to engage the rack commanding the translation of the additional guide.

In this example, the driving block is adapted to guide the sliding of both guides 24*b* and 25*b* and the additional guides along paths 24*a* and 25*a*. The driving block may include one or more idler wheels hinged to the mobile module 23*b* and 23*c* and adapted to go in contact with the guides 24*b* and 25*b* and/or with the additional guides. The driving block also may include a pilot profile integral with the module 23*b* or 23*c* and placed on the opposite side to the idler wheels with respect to the arched guide 24*b* and 25*b* so that the arched guide 24*b* and 25*b* is placed between them. One or more additional idler wheels hinged to the arched guide 24*b* and 25*b* and between so as to be interpose and go in contact with the pilot profile and the additional guide and enclose the additional guide between the wheels and the additional wheels may also be included.

By virtue of this arrangement, each mover 24 and 25 is capable of moving the additional arched guide with a speed twice that of the guide 24*b* and 25*b*. The driving mechanism moves the guide 24*b* and 25*b*, owing to the driver profile and idler wheel, along the trajectories 24*a* and 25*a*. Therefore, the additional idler wheel, hinged to the additional arched guides 24*b* and 25*b* and in contact with the pilot profile, start to rotate in a direction opposite to that of the arched guides 24*b* and 25*b*. In turn, the additional rotation of the additional wheels causes a rotation of the additional arched guide on the opposite direction to the additional wheels and, therefore, concordant with the guide 24*b* and 25*b*. Thus, the additional arched guide is moved with a speed twice that of the guide 24*b* and 25*b* as given by the sum of the speed of the guide 24*b* and 25*b* and the speed of the additional idler wheels.

In yet another embodiment, inside the casing 23, the gantry 20 includes a sensor movement system 26 located between the detector 22 and the cart 24*c* that is able to translate the detector 22 keeping sensitive surface 22*a* almost perpendicular to the axis of propagation 21*a*.

The sensor movement system 26 is adapted to translate the detector 22 along a moving axis 26*a* substantially perpendicular to the axis of propagation 21*a* and, in detail, perpendicular to the axis of expansion 20*a*. In one embodiment, the sensor movement system 26 is adapted to translate the detector 22, with respect to a position in which the axis of propagation 21*a* intersects the center of the sensitive surface 22*a*, of a quantity between about ±300 mm and about ±10 mm. The quantity may also be within about ±150 mm and about ±50 mm.

The sensor movement system 26 includes a moving guide 26*b* defining the flapping axis 26*a*, a moving cursor 26*c* supporting the detector 22 and able to slide along the moving guide 26*b*. The sensor movement system 26 also includes a moving motor 26*d* suitable to command the motion of the moving cursor 26*c* along the moving guide 26*b*. The moving motor 26*d* may be electric or any other type of suitable motor.

The gantry 20 including at least the source 21, the detector 22 and the internal movers 24 and 25 are controlled by the control station 30. An operator may give commands through the station 30.

In one embodiment, the control station 30 includes an interface 31 suitable to permit the operator to interact with the device 1, an electronic circuit board 32 or other similar element suitable to be placed in data transfer connection with the various components of the device 1 so as to control the functioning thereof. The control station 30 may include a power supply group 33 suitable to supply electricity to the various components. A housing 34 may also be included, which is suitable to at least partially house the elements and defining the main axis of extension 30*a*, preferably, substantially perpendicular to the floor defining a surface upon which the device 1 is disposed (in other words substantially parallel to the gravitational gradient). The housing may have a cross-section with dimensions that practically are the same in at least some respects as those of the gantry 20.

The power supply unit 33 may include a battery and, alternatively or in addition thereto, connection cables suitable to permit the powering of the device an external electricity grid.

The interface 31 includes at least one screen 31*a* suitable to display the results of the analysis and/or to monitor the functioning of the device 1. Also, the interface 31 may include an alphanumerical key board 31*b* or any other type of active interface suitable to permit the operator to control the device.

In one embodiment, the screen 31*a* is hinged to the housing so that when used, it is rotated so as to assume an optimal inclination in order to be read or, when not used, rotated so as to be practically entirely inserted in a specific seat 34*a* obtained in the housing 34. In one embodiment, in order to maintain the inclination, a stand 31*c* or other similar element suitable to prop the screen in the desired position may be attached to the screen 31*a*.

In addition to the aforementioned elements, the control station 30 may include a linear actuator 35 suitable to move the articulated arm 40 and, therefore, the gantry, preferably along a direction practically parallel to the axis of extension 30a. One or more pivoting wheels 36 suitable to move the device 1 may also be a part of the control station 30. The control station 30 also includes a handle 37 suitable to be held by the operator so as to guide the movement of the device 1. Further, one or more stop devices 38 suitable to abut against a floor surface preventing the movement of the device 1 may be part of the control station 30. In one example, the devices 38 include linear actuators suitable to extend so as to abut with the floor preventing the movement of the device 1 and, alternatively, to contract to distance themselves from the floor surface and permit the movement of the device 1.

As shown in the figures, structurally positioned between the gantry 20 and station 30, the radiological imaging device 1 has an articulated arm 40 which moves the gantry 20 in relation to the control station 30. There is also a compensating member 50 suitable to rotate the gantry 20 with respect to the station. The articulated arm 40 and the compensating member 50 are controlled by the control station 30 and, more precisely, according to commands given by the operator through the station 30.

The compensating member 50 is able to rotate the gantry 20 about an axis substantially parallel to the preferred axis of expansion 20a in order to rotate, together with the curved inner guide, the source 21 and the detector 22 of 360° and, therefore, to perform imaging at 360°. The compensating member 50 is able to rotate the curved module 21b and, therefore, the gantry 20 through an advancing angle between about 100° and about 200°. The rotation of the gantry may also be through an advancing angle between about 145° and about 180° and, the rotation may also be equal to about 160°.

In one embodiment, the compensating member 50 includes at least one rack 51 disposed at least one of the base surfaces 20d and having a trajectory extending substantially in the shape of an arc of a circumference having its center on the preferred axis 20a and extension substantially equal to the advancing angle. At least one driving body 52 having a toothed wheel or other similar device suitable to engage with the rack 51 and a motor (not shown) is able to control the rotation of toothed wheel and, then, of the gantry 20. The motor may be an electric motor or other suitable type of motor.

In one embodiment, the compensating member 50 includes at least two racks 51, each one placed on the same side of the gantry 20 (i.e. a base surface 20d), and two driving bodies 52 each one associated with a corresponding one of racks 51 of a base surface 20d.

The arm 40 moves the gantry 20 defining, for the device 1, an operating configuration (FIG. 1a) wherein the gantry 20 and, then, the casing 21 are distanced from the control station 30. The arm 40 also moves the gantry into a rest configuration (FIG. 1b) wherein the gantry 20 and the casing 21 are alongside the station 30 thereby limiting the overall dimensions of the imaging device 1. The arm 40 thus enables movement of the gantry 20 to and from those positions (FIGS. 1a and 1b), as well as to positions intermediate those positions.

Figure 1B:
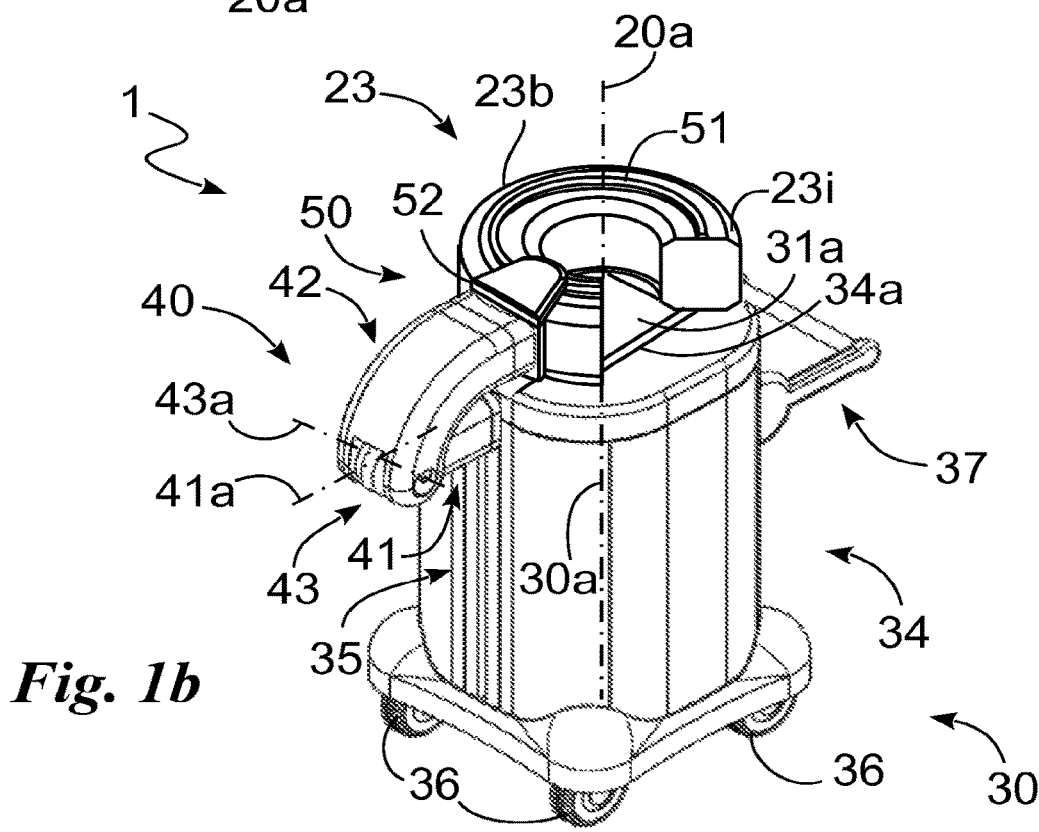

In the rest configuration, the gantry 20, as illustrated in FIG. 1b, has the preferred axis 20a substantially parallel and, more specifically, substantially coinciding with the main axis of extension 30a, and even more specifically, has a base surface 20d substantially adjacent to the housing 34.

The articulated arm 40 may include a first body 41 joined to the control station 30 and a second body 42 joined to the gantry 20. The second body 42 may be joined to the driving body 52. The articulated arm 40 also includes a hinge 43 suitable to command a relative rotation between the bodies 41 and 42 along an axis of rotation 43a, preferably substantially transverse, more preferably, substantially perpendicular to the axis of extension 30a.

The first body 41 may be telescopic and also may include a linear actuator suitable to vary the distance between the gantry 20 and the control structure 30 by virtue of a variation of its extension. In one embodiment, the first body 41 is suitable to vary its extension in a lengthening direction 41a substantially transverse and, more particularly, perpendicular to the main axis of extension 30a and, even more particularly, substantially perpendicular to the axis of extension 30a and to the axis of rotation 43a.

The second body 42 has an arched shape or shape such as to permit, in the closed configuration, the second body 42 to overlap the first 41.

Additionally, the articulated arm 40 has rotation mechanism 44 positioned between the driving body 52 and the second body 42 suitable to rotate the gantry 20 in relation to the second body 42 and, thus, to the control station 30. In one embodiment, the rotation mechanism 44 rotates the gantry 20 in relation to an axis of rotation 44a substantially transverse or perpendicular to the preferred axis of expansion 20a.

Additionally, the articulated arm 40 may include a quick release system, not shown in the figure, able to quickly separate the gantry 20 from the rest of the radiological imaging device 1 and, in detail, from same articulated arm 40. The quick release system is disposed between the rotating mechanism 44 and the driving body 52 and includes connectors, for example sliding contacts, suitable to electrically connect/disconnect the gantry 20 to/from the device 1. This allows a data connection between the components when in the connected state.

Also, the radiological imaging device 1 may include a carriage 60 suitable to be joined to the control station 30 so as to permit the movement of the device 1 up or down stairs or along other non-level or irregular surfaces. In one embodiment, the carriage 60 (FIG. 3) includes a support 61 suitable to be joined to the control station 30. The carriage may also include restrains 62, such as ropes and fasteners, suitable to attach the support 61 to the control station 30 and, therefore, to become part of the overall the device 1. Also, movement devices 63 suitable to permit the movement of the carriage 60 may also be a part of the carriage.

In one example, the support 61 includes a first sheet 61a suitable to come into contact with the device 1 in correspondence of the handle 37, and a second sheet 61b integral with the first sheet 61a and suitable to be inserted between the pivoting wheels 36 and a floor surface. There may also be at least one profile 61c suitable to provide stability to the support 61. The support 61 may include a grip 61d suitable to be held by an operator permitting the movement of the carriage 60 and, therefore, the device 1.

The movement devices 63 may include wheels 63b positioned at the junction point of the sheets 61a and 61b. Also, the movement devices include at least one caterpillar track 63a positioned at the first sheet 61a and suitable to permit the movement of the device up or down stairs or on uneven floors or similar surfaces.

By way of example only, and not by way of limitation, the functioning of the radiological imaging device described above in a structural sense is as follows.

Initially, the radiological imaging device 1 is in the rest position wherein the gantry 20 and the casing 21 are alongside the control station 30 and, in particular, the preferred axis of expansion 20a substantially coincides with the main axis of extension 30a and a base surface 20d is practically adjacent to the housing 34 (FIG. 1a).

At the moment of use, the operator positions the assembly composed of the control station 30 and gantry 20 on the carriage 60 positioning the pivoting wheels 36 on the second sheet 61b and resting the housing 34 against the first sheet 61a.

Using the restrains 62, the operator attaches the control station 30 to the carriage 60 and, using the movement devices 63, transports the radiological imaging and moves device 1 in proximity of the patient.

At this point the operator distances the carriage 60 from the rest of the device 1, and configures the device 1 into the operating position (FIG. 1b).

After completing such operations, the operator translates the station/gantry assembly by virtue of the pivoting wheels 36 so that at least part of the portion to be analyzed traverses the angular perimetric aperture 21a and enters the analysis zone 20c.

Figure 2:
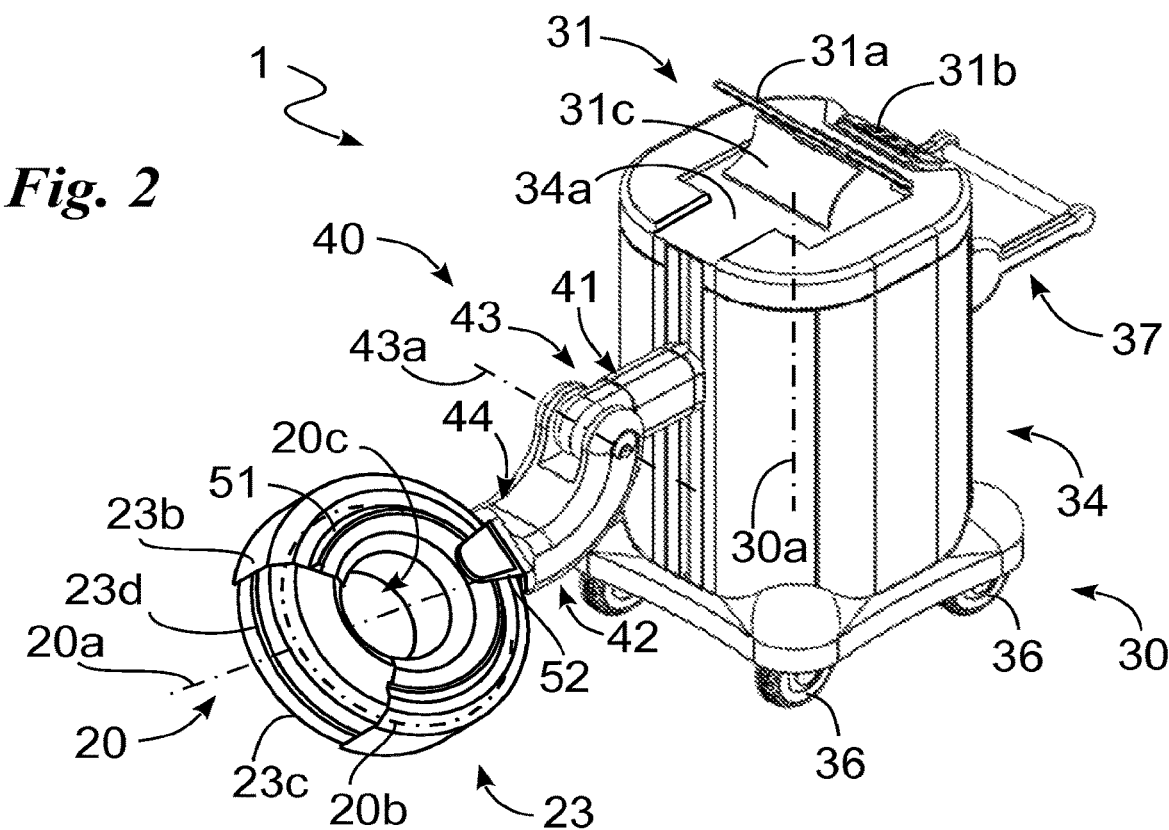
FIG. 2 shows another configuration of an imaging device.

Now, the operator controls, through the control station 30, the passage of device 1 in the work configuration and, therefore, the kinematic mechanism 23d controls the additional module 23c, which starts to protrude from the arched module 23b until the gantry 20 defines an angular extension equal to about 360° (FIGS. 2, 4b and 5b).

The movement of the additional module 23c causes a movement of the inner guide 24b that is then placed in the opposite side of the outer guide 25b with respect to the preferred axes 20a (FIG. 4b).

Now, the operator operates the control station 30 to specify a desired angular position of the source 21 and of the detector 22. As a result, the compensating member 22 and/or the carts 24c and 25c rotate, around on the axis of expansion 20a, the source 21 and the detector 22 until they reach such position.

At this point, either automatically or in response to a command from the operator control using the control station 30, the source 21 starts to emit X-rays. In some example embodiments, the linear actuator 35 moves the gantry 20 while the source 21 emits X-rays making it possible to perform the radiological imaging of an extensive portion.

The radiological imaging device 1 permits significant advantages. In view of the foregoing, the radiological imaging device 1 has significantly reduced overall dimensions and is therefore easy to transport. The reduced dimensions and ease of transport has been innovatively achieved by virtue of the rest configuration in which the gantry 20 can be in contact with the control station 30, making it possible to achieve a significant reduction in the overall dimensions compared to the prior art devices.

Specifically, by positioning the gantry 20 with the preferred axis of expansion 20a substantially coinciding with the axis of extension 30a and with the base 20 substantially adjacent to the housing 34 the cross-section of the entire device is reduced to that of the control station 30 as shown in FIG. 1b.

Additionally, the carriage 60 contributes to the aforementioned improved transportability, owing to its ability to move the device 1 up and down stairs or steps or on any other surface by virtue of the caterpillar tracks 63b.

Moreover, by virtue of the module 21b and the compensating member 50, it is possible to have a gantry 20 that is open, at least in part, at aperture 21a and able to perform scanning along any desired span within (or above) 360°. In one example, owing to the aperture 21a of the open gantry 20, the limbs of animals can, without being moved, be positioned for examination in such zone 20c.

Furthermore, the presence of the quick release system allows rapid separation of the gantry 20 from the device 1 and, therefore, reduces the likelihood that unexpected movements of, for example, an animal (e.g. kick of a horse) will damage the radiological imaging device 1 or the animal itself.

Further protection against damage is provided by the elastomeric coating 21d of the gantry 20.

One of ordinary skill in the art will appreciate that not all radiological imaging devices have all these components and may have other components in addition to, or in lieu of, those components mentioned here. Furthermore, while these components are viewed and described separately, various components may be integrated into a single unit in some embodiments.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A radiological imaging device, comprising:
a gantry having a casing housing a source configured to emit radiation and a detector configured to receive the radiation, the casing of the gantry includes a first curved module and a second curved module, the casing is configured to move between an open configuration and a closed configuration, wherein in the open configuration the casing presents an annular shape opened in order to define an angular perimetric aperture and in the closed configuration the casing has no angular perimetric aperture, and the first and second curved modules support the source and detector;
a control station configured to control the functioning of the source and the detector;
an articulated arm configured to move the gantry in relation to the control station defining, for the radiological imaging device, an operating configuration wherein the gantry is distanced from the control station and a rest configuration wherein the gantry is alongside the control station limiting the overall dimensions of the radiological imaging device.

2. The radiological imaging device of claim 1, wherein the gantry defines a preferred axis of expansion, the control station defines a main axis of extension, and in the rest configuration, the preferred axis of expansion is substantially parallel to the main axis of extension.

3. The radiological imaging device of claim 2, wherein, in the rest configuration, the preferred axis of expansion substantially coincides with the main axis of extension.

4. The radiological imaging device of claim 1, wherein the articulated arm includes a first body joined to the control station, a second body joined to the gantry, and at least one hinge configured to command the relative rotation between the bodies along an axis of rotation.

5. The radiological imaging device of claim 4, wherein the axis of rotation is substantially perpendicular to the main axis of extension.

6. The radiological imaging device of claim 4, wherein the articulated arm includes a rotation mechanism positioned between the gantry and second body so as to rotate the gantry in relation to the second body.

7. The radiological imaging device of claim 6, wherein the axis of rotation is perpendicular to the preferred axis of expansion.

8. The radiological imaging device of claim 1, further comprising a control station configured to control the functioning of the source and the detector.

9. The radiological imaging device of claim 8, wherein the control station includes a linear actuator configured to move the articulated arm and the gantry in a direction substantially parallel to the main axis of extension.

10. The radiological imaging device of claim 8, further comprising a carriage configured to be joined to the control station permitting the movement of the radiological imaging device.

11. The radiological imaging device of claim 10, wherein the carriage includes at least one caterpillar track.

12. The radiological imaging device of claim 1, wherein when the gantry is in the rest configuration the casing has substantially a C shape.

13. The radiological imaging device of claim 1, wherein when the gantry is in the working configuration, the casing has an angular extension of 360°.

14. A radiological imaging device, comprising:
a gantry configured to perform the radiological imaging and including a casing housing a source configured to emit radiation and a detector configured to receive the radiation, and the casing includes a first curved module and a second curved module;
a control station configured to control the functioning of the source and the detector; and
an articulated arm having a first body joined to the control station, a second body joined to the gantry, and at least one hinge suitable configured to command the relative rotation between the bodies along an axis of rotation, and the articulated arm includes a rotation mechanism positioned between the gantry and second body so as to rotate the gantry in relation to the second body, the articulated arm is configured to move the gantry in relation to the control station defining, for the radiological imaging device, an operating configuration wherein the gantry is distanced from the control station and a rest configuration wherein the gantry is alongside the control station limiting the overall dimensions of the radiological imaging device.

15. The radiological imaging device of claim 14, wherein the gantry defines a preferred axis of expansion, the control station defines a main axis of extension, and in the rest configuration, the preferred axis of expansion is substantially parallel to the main axis of extension.

16. The radiological imaging device of claim 15, wherein, in the rest configuration, the preferred axis of expansion substantially coincides with the main axis of extension.

17. The radiological imaging device of claim 16, wherein the axis of rotation is substantially perpendicular to the main axis of extension.

* * * * *